United States Patent
Carrault et al.

(10) Patent No.: US 11,464,458 B2
(45) Date of Patent: Oct. 11, 2022

(54) SYSTEM FOR EVALUATING THE MATURATION OF A PREMATURE BABY

(71) Applicants: Université de Rennes 1, Rennes (FR); CHU de Rennes, Rennes (FR); Institut National de la Santé et de la Recherche Médicale (INSERM), Paris (FR)

(72) Inventors: Guy Carrault, Saint-Briac (FR); Nadine Khodor, Châtillon (FR); Patrick Pladys, Noyal-sur-Vilaine (FR); Mathieu Kuchenbuch, Rennes (FR)

(73) Assignees: UNIVERSITÉ DE RENNES 1, Rennes (FR); CHU DE RENNES, Rennes (FR); INSTITUT NATIONAL DE LA SANTÉ ET DE LA RECHERCHE MÉDICALE (INSERM), Paris (FR)

( * ) Notice: Subject to any disclaimer, the term of this patent is extended or adjusted under 35 U.S.C. 154(b) by 322 days.

(21) Appl. No.: 16/643,866

(22) PCT Filed: Sep. 5, 2018

(86) PCT No.: PCT/FR2018/052165
§ 371 (c)(1),
(2) Date: Mar. 3, 2020

(87) PCT Pub. No.: WO2019/048775
PCT Pub. Date: Mar. 14, 2019

(65) Prior Publication Data
US 2020/0281487 A1    Sep. 10, 2020

(30) Foreign Application Priority Data
Sep. 5, 2017    (FR) ...................... 1700895

(51) Int. Cl.
*A61B 5/00* (2006.01)
*G16H 50/30* (2018.01)
(Continued)

(52) U.S. Cl.
CPC ........ *A61B 5/7275* (2013.01); *A61B 5/02405* (2013.01); *A61B 5/352* (2021.01);
(Continued)

(58) Field of Classification Search
CPC ... A61B 5/7275; A61B 5/02405; A61B 5/352; A61B 5/369; A61B 5/743;
(Continued)

(56) References Cited

U.S. PATENT DOCUMENTS 7,515,948 B1 * 4/2009 Balberg ............... A61B 5/0095
600/338
2018/0070886 A1 * 3/2018 Fairchild ............. A61B 5/1455

FOREIGN PATENT DOCUMENTS

WO    2015142046 A1    9/2015

OTHER PUBLICATIONS

Bartolo Luque, et al:, "Horizontal visibility graphs: exact results for random time series", Cornell University Library, Feb. 24, 2010, XP080393539.
(Continued)

*Primary Examiner* — Catherine M Voorhees
(74) *Attorney, Agent, or Firm* — Cantor Colburn LLP

(57) ABSTRACT

The invention relates to a non-invasive system for determining the maturation of a baby, which comprises a module for sampling a cardiac or electroencephalographic signal from a baby and advantageously performs a conversion of a plurality of temporal samples derived from the cardiac signal or from the electroencephalic signal into a visibility graph, then a determination of at least one index on the basis of this visibility graph, a comparison of at least one deter-
(Continued)

(a)

(b)

mined index with one or more statistical indices representative of the maturation of a plurality of babies and a visual representation of a distance between at least one determined index and the statistical indices.

2 Claims, 3 Drawing Sheets

(51) Int. Cl.
  *A61B 5/024* (2006.01)
  *A61B 5/369* (2021.01)
  *A61B 5/352* (2021.01)
  *A61B 5/366* (2021.01)
(52) U.S. Cl.
  CPC .............. *A61B 5/369* (2021.01); *A61B 5/743* (2013.01); *G16H 50/30* (2018.01); *A61B 5/02411* (2013.01); *A61B 5/366* (2021.01); *A61B 2503/02* (2013.01); *A61B 2503/045* (2013.01)
(58) Field of Classification Search
  CPC . A61B 5/02411; A61B 5/366; A61B 2503/02; A61B 2503/045; G16H 50/30
  See application file for complete search history.

(56) References Cited

OTHER PUBLICATIONS

Elina Helander, et al., "Comparison of linear and non-linear heart rate variability indices between preterm infants at their theoretical term age and full term newborns", IFMBE proceedings, Jun. 13, 2017, XP055525206.
Elke Longin, "Maturation of the autonomic nervous system: differences in heart rate variability in premature vs term infants", Journal of Perinatal Medicine, vol. 34, No. 4, Jan. 1, 2006, XP055480619.
International Search Report for corresponding application PCT/FR2018/052165 filed on Sep. 5, 2018; dated Nov. 30, 2018.
Madl Tamas, "Network analysis of heart beat intervals using horizontal visibility graphs", 2016 Computing in Cardiology Conference, Sep. 11, 2016, pp. 733-736, XP033071266.
Nadine Khodor, "Evaluation de la Maturation des bebes prematures par graphe de visibilite", INSERM, Sep. 2017.
Patural H, et al., "Birth prematurity determines prolonged autonomic nervous system immaturity", Clinical Autonomic Research, vol. 14, No. 6, Dec. 1, 2004, pp. 391-395, XP019383624.
Shany Eilon, et al. "In and ex utero maturation of premature infants eletroencephaloraphic indices", Clinical Neurophysiology, vol. 125, No. 2. Jul. 30, 2013, pp. 270-276, XP028669248.

* cited by examiner

SYSTEM FOR EVALUATING THE MATURATION OF A PREMATURE BABY

1. FIELD OF THE INVENTION

The present invention relates to a system for evaluating a level of maturation of a premature baby using statistical elements.

2. PRIOR ART

It is known that the autonomic nervous system has an effect on many organs, including the heart, and that cardiac variability reflects the influence of the autonomic system on the heart. The variability in cardiac frequency, also called HRV, is a practical, non-invasive and reproducible way of measuring the functioning of the autonomic nervous system. Although the heart is relatively stable, the time between two heartbeats may be very different. HRV is the variation over time in consecutive heartbeats. It is supposed to correspond to the equilibrium between the sympathetic and parasympathetic influences on the intrinsic rhythm of the sinoatrial node. Measurement of HRV is of great interest in medical practice as it allows cardio-metabolic risk to be predicted and evaluated.

In fetuses, analysis of cardiac rhythm is a useful way of detecting anomalies that may occur either during pregnancy, or during birth. The analysis of fetal cardiac rhythm is generally based on four criteria: basic rhythm, the variability in this basic rhythm, accelerations, and the presence of slowing where appropriate.

Other tools are known and are employed to evaluate the maturation of fetuses. Thus, obstetric ultrasonography and Doppler ultrasonography assist in establishing biophysical scores for evaluating fetal state.

Other means such as, for example, amniocentesis and fetal blood sampling exist, but they have the drawback of being invasive.

Although the maturation of a fetus may be evaluated by the means described above, it is also important and appreciable to be able to evaluate the maturation of a baby after birth. The evaluation of the maturation of a premature newborn turns out to be invaluable and could be improved.

3. SUMMARY OF THE INVENTION

The invention allows at least certain drawbacks of the prior art to be improved by providing a system for determining an index allowing the maturation of babies to be evaluated objectively.

Thus, the invention relates to a system for determining the maturation of a baby, comprising a module for sampling a cardiac signal of the baby (acquisition of the electrocardiographic signal of the baby and its conversion into a new series) in order to produce a sequence of time samples respectively defining time intervals that separate two successive heartbeats, the system especially comprising:
- a module for converting a plurality of time samples of the cardiac signal of the baby into data representative of a visibility graph instantiated in the system,
- a module for determining at least one index (or value) from data representative of the instantiated visibility graph,
- an analyzing module suitable for comparing this at least one determined index with one or more statistical indices representative of the maturation of a plurality of babies, and,
- a module for visually representing a quantity representative of a distance between the at least one determined index and the plurality of predefined statistical indices representative of the maturation of a plurality of babies.

4. LIST OF FIGURES

The invention will be better understood, and other particularities and advantages will become apparent, on reading the following description, the description making reference to the appended drawings, in which.

5. DETAILED DESCRIPTION OF EMBODIMENTS OF THE INVENTION

Figure 1:
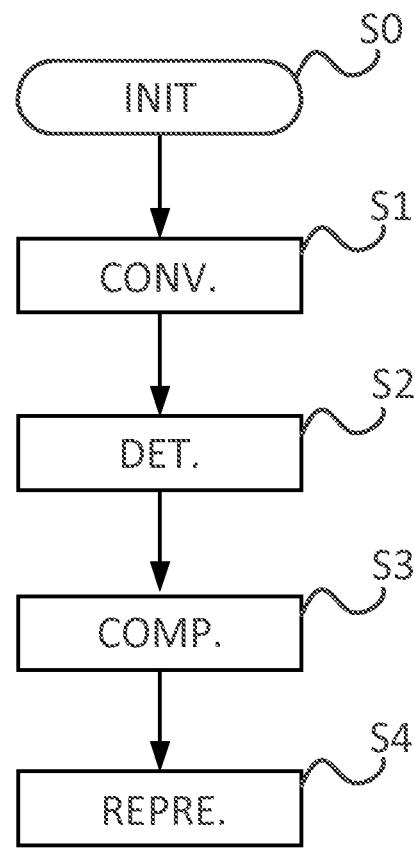
FIG. 1 is a chart showing steps of the method according to one particular and nonlimiting embodiment of the invention.

FIG. 1 is a chart showing steps of a method implemented by a system according to the invention.

Step S0 is a step of initializing the method at the end of which a system implementing the method is configured to work with data representative of a cardiac signal of a baby, which consists of a succession of RRI time samples respectively defining time intervals that separate two successive heartbeats. In step S0, apart from the initialization and configuration of the various elements of the system, analogue signals sampled during an electrocardiogram carried out on the baby subject to an analysis aiming to determine its degree of maturation are recorded and preprocessed. RRIs intervals are extracted by implementing an algorithm similar to that of Pan and Tompkins, which detects QRS complexes using digital analyses of the slope, of the amplitude and of the width of the ECG signal. Filtering coefficients specifically tailored to newborns are employed. According to one particular and nonlimiting embodiment of the invention, a moving window of five minutes with 50% overlap is used. The parameters of the cardiac variability are computed in time segments (time intervals) of five minutes selected to be the segments that are the most static each thirty minutes. According to one embodiment of the invention, Kaplan filters are used to remove certain artefacts from the digitized RRI series.

At the end of the configuration of which step S0 consists, a sequence of RRI data is stored in a memory of the system implementing the method.

Step S1 consists in converting the plurality of RRI time samples thus made available in memory into data representative of a visibility graph VG. Each of the points of the RRI time series is converted into one node of the visibility graph then instantiated in the memory of the system. Connectivities between the various nodes are determined via a visibility criterion such that:

any two nodes $(t_i, y_i)$ and $(t_j, y_j)$ become connected if another node $(t_k, y_k)$ such that $t_i < t_k < t_j$ meets the following criterion:

$$y_k < y_i + (y_i - y_j)\frac{t_j - t_k}{t_j - t_i} \qquad [1]$$

The number of links of $(t_i, y_i)$ is represented by the degree k(i).

A visibility graph representing an RRI time series is characterized by its degree sequence (i.e. the number of links connected to a node), the mean MD_V of the sequence and the degree distribution. Luque et al. [B. Luque et al, "Horizontal visibility graphs: exact results for random time series", ArXiv10024526 Cond-Mat Physics, February 2010] introduced horizontal visibility HV, which is a subset of the visibility graph VG, and in which $(t_i, y_i)$ and $(t_j, y_j)$ are connected if:

$$\forall t_K \in t_i, t_j : y_i > y_k \text{ and } y_j > y_k \quad [2]$$

A new visibility graph VD may then be obtained by finding the difference between the links of the visibility graph VG and the links of the horizontal visibility HV. Thus, the mean of the sequence of VD is equal to:

$$MD\_D = MD\_V - MD\_H$$

According to one embodiment of the invention, coefficients (indices) characterizing the visibility graph VG are extracted therefrom. This amounts to saying that one or more indices that characterize this network of nodes are computed depending on the connections between the nodes of the network ensuing from the visibility graph VG. It may be a question of assortativity ASSOR or even of transitivity TRANS, by way of nonlimiting examples. This method is valid provided that the same durations of observation are used to define the pre-recorded parameters representing a cohort of babies and the one or more indices characterizing the maturity of one baby which is considered in isolation.

Step S2 is a step of determining one or more indices that characterize a network defined by all of the obtained nodes. For example, indices of assortativity ASSOR and transitivity TRANS are determined. Assortativity ASSOR is a global measure equivalent to the Pearson correlation between the degrees of each of the pairs of nodes; it provides information on the dynamic behavior of the network; and transitivity TRANS quantifies to what point the neighbors of a node are connected and therefore reflects the density of the network.

Step S3 consists in comparing at least the index determined in step S2 with one or more statistical indices (ATi, Pmi, Epi) representative of the maturation of a plurality of babies. According to one embodiment of the invention, the indices ATi are statistical indices that represent a cohort of babies born at term, the indices Pmi are statistical indices that represent a cohort of babies born prematurely and the indices Epi are statistical indices that represent a cohort of babies born extremely prematurely. These indices are determined from a cohort representative of a population of babies, prior to an analysis implementing the method but aimed at one baby subject considered in isolation (aiming to determine its degree of maturity), and by proceeding according to the method for each of the subjects of the cohort in question.

Step S4 consists in visually representing a distance D or a quantity representative of this distance D between at least one determined index and a plurality of indices defined beforehand by statistical analysis, which indices are stored in the memory of the system.

The representation may be graphical and employ, by way of example, a star plot or a point superposed on regions of a space that are respectively representative of degrees of maturity, or a bar graph indicating a degree of maturity between "at term" and "very premature" extremes. This list of examples is of course not exhaustive.

According to one particular and nonlimiting embodiment of the invention, the method for representing visually is based on one or more graphs or plots which show a point superposed on one or more regions representative of a state, such as, for example, a degree of prematureness or of matureness and making possible a classification or a tendency among or toward predetermined degrees of maturation.

Advantageously, the representation uses so-called "box-and-whisker" plots, which are commonly used in the representation of statistical quantities.

In other words, step S3 consists in comparing the indices that are determined in step S2 and obtained via operations employing a visibility graph (and the corresponding network of nodes) and indicators determined beforehand and stored precedingly in the memory of the system, describing the variability in cardiac frequency (time, frequency and non-linear indices). These indices are computed from cohorts of premature babies and of babies certain of which are born at term, representative of the population in terms of maturation, before the described analysis according to the method of the invention applied to one newborn subject considered in isolation.

Step S4 consists in visually representing a distance D or a quantity representative of this distance D between the one or more indices determined using the method according to the invention and a determined set of similar predefined and pre-recorded indices.

According to one particular and nonlimiting embodiment of the invention, the method for representing visually is based on a statistical procedure that uses an orthogonal linear transformation to convert all the indices obtained from babies born at term into a new space in which the information is summarized while keeping the greatest possible variance, allowing one or more regions representative of a state, such as, for example, a degree of prematureness or matureness, to be seen. Premature babies are then projected onto this space as additional individuals, making possible a classification among predetermined degrees of maturation.

Advantageously, the representation uses so-called "box-and-whisker" plots, which are commonly used in the representation of statistical quantities.

Figure 2:
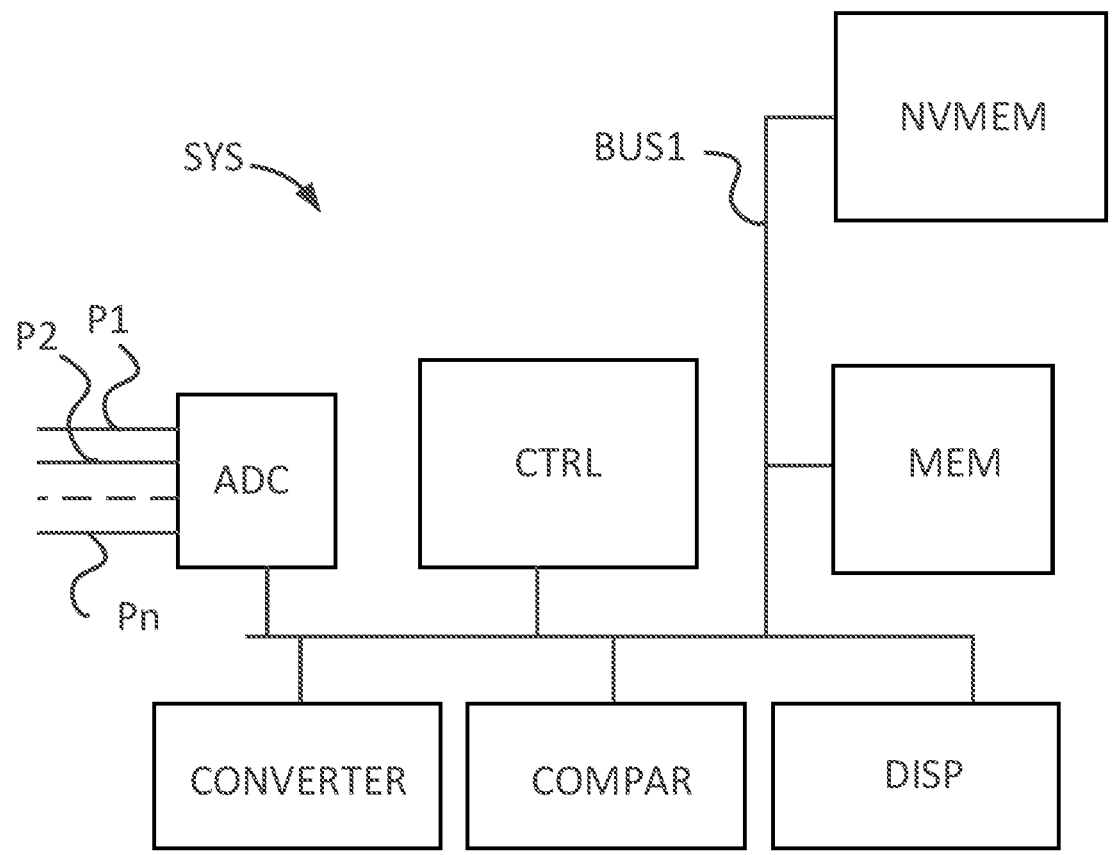
FIG. 2 shows a system suitable for implementing the method illustrated by FIG. 1, according to one particular and nonlimiting embodiment of the invention.

In FIG. 2, the modules shown are functional units, which may or may not correspond to physically distinguishable units. For example, these modules or certain thereof are integrated into a single component, or consist of functionalities of a given software package. In contrast, according to other embodiments, certain modules are composed of physically separate entities.

FIG. 2 shows a system SYS for determining the maturation of a baby on the basis of sampling of a cardiac signal of the baby subject of the analysis. The system SYS comprises a control unit suitable for carrying out conventional operations of acquiring and processing signals and analogue and digital data, computational statistical and digital analyzing operations, and any other operation conventionally carried out by a computer. The control and analysis unit CTRL comprises one or more internal microcontrollers and an interface enabling connection to a fast, bidirectional and multiplexed shared bus BUS1. The system SYS also comprises a module ADC for converting analogue signals into digital data, a computing and digital-analysis module CONVERTER configured to carry out operations on data instantiating one or more visibility graphs, a module COMPAR configured to compare determined indicators or indices with statistical indicators or indices stored beforehand in the system SYS, a working memory module MEM suitable for temporarily storing data used by the statistical operations and a nonvolatile memory module suitable for storing software code corresponding to programs and algorithms and to predefined statistical data, recorded beforehand and resulting from statistical operations carried out prior to the implementation of the method according to the invention. The module ADC is able to convert analog signals delivered by a plurality of probes P1, P2, . . . Pn used to perform electrocardiograms, and in particular suitable for the practice of electrocardiograms on a newborn. The module ADC also comprises one or more filters configured to remove parasitic noise during sequences of recording the constituent signals of an electrocardiogram. Of course, the system SYS also comprises all of the conventional elements of a microcontroller-comprising system, such as, by way of nonlimiting example, supply circuits, power interfaces, one or more clock circuits, one or more zeroing circuits, input/output ports, switch inputs, modules for managing and sharing buses and memory modules.

The system SYS lastly comprises a display module DISP comprising a high-resolution screen suitable for representing graphical and textual objects in color, and provided with an audio output interface comprising a sound-generating device.

All of the constituent elements of the architecture of the digital core of the system SYS are not described in more detail here, because they are well known to those skilled in the art of digital devices for processing signals and computing, and in so far as these elements are not useful to the comprehension of the present invention.

When the system SYS is used to implement the method according to the invention, analogue signals representative of the heartbeats of a premature baby are detected during an electrocardiogram and transmitted to the module ADC via the probes P1, P2, . . . Pn. These signals are then processed by the module ADC and converted into a sequence of RRI time samples respectively defining time intervals that separate two successive heartbeats of a premature baby, subject to an analysis with a view to determining its degree of maturation. The RRI time samples are stored in a region of the random-access memory MEM reserved for this purpose.

The conversion module CONVERTER then converts the plurality of RRI time samples into data representative of the visibility graph VG described above and determines at least one indicator from these data. The module COMPAR makes comparisons between at least the indicator determined beforehand and one or more statistical indices representative of the maturation of a plurality of babies certain of which were born at term, these statistical indices being stored beforehand in a dedicated region of the non-volatile memory NVMEM. Each of the modules CONVERTER, COMPAR and DISP comprises its own control and processing unit, similar to that already described and implemented in the module CTRL. The module CTRL however supervises all of the operations of the system, especially by executing corresponding algorithms using executable routines the code of which is stored in non-volatile memory NVMEM.

Once the operations described above have been carried out in succession under software control and via implementation of the control module CTRL, the visual representation module DISP displays a quantity representative of a distance D, determined by the module COMPAR, between at least the index determined by the module CONVERTER working on the visibility graph and the plurality of statistical indices recorded and stored beforehand.

Advantageously, the module DISP displays one or more graphs or plots allowing a point defining the maturation of the premature baby subject to the analysis to be defined with respect to a set of points representative of maturation levels determined beforehand and stored beforehand in the system.

According to one variant, the module DISP, under control of the module CTRL, displays the maturation level determined by the method and associated with the baby subject to the analysis by highlighting it on a scale of predefined maturation values.

Figure 3:
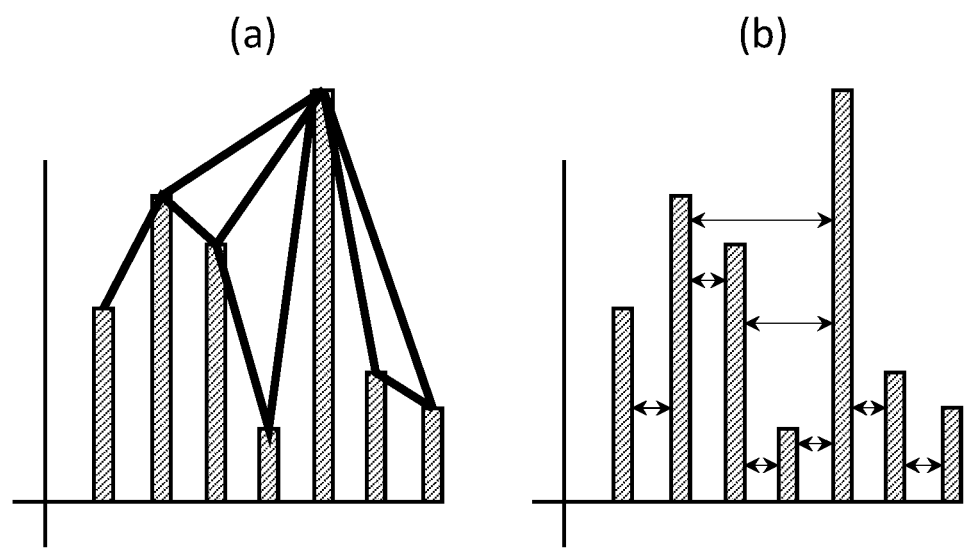
FIG. 3 illustrates the principle of visibility graphs, this principle being cleverly used in the method for evaluating the maturity of a baby according to the invention.

FIG. 3 comprises two schematic representations of visibility graphs such as used by the described method.

The left-hand side of FIG. 3, which is referenced a), illustrates a vertical visibility graph. Two arbitrary points $(t_i, y_i)$ and $(t_j, y_j)$ of the time series will become two connected nodes of the associated graph (network of nodes) if an arbitrary point $(t_k, y_k)$ placed therebetween meets the following criterion:

$$y_k < y_i + (y_i - y_j)\frac{t_j - t_k}{t_j - t_i}$$

The right-hand side of FIG. 3, which is referenced b), illustrates a horizontal visibility graph in which two arbitrary points $(t_i, y_i)$ and $(t_j, y_j)$ of the time series will become two connected nodes of the associated graph (network of nodes) if they are higher than all the points therebetween.

The visibility condition is therefore the following:

$$\forall c \in [a,b]\ y_a > y_c \text{ and } y_b > y_c$$

Other parameters may be computed with the visibility-graph method, i.e. degree distribution. Theoretically, a degree distribution DD is the probability that any point has a visibility index x. To compute it, the number of points having a degree of visibility of x is computed and divided by the total number of points.

According to one preferred embodiment of the invention, these degrees are calculated for analysis time windows of thirty seconds.

It is then possible to obtain a table of DD for each analysis window, i.e. for example one hundred and twenty tables for one hour of recording. These tables return the count of the indices and not a probability. The available data are then multiplied by a coefficient in order to normalize the results on the basis of a recording of one hour.

Thus, visibility indices such as, by way of example, the assortativity ASSOR, the transitivity TRANS or the mean degree of the sequence, are computed from these visibility graphs and corresponding networks of nodes. Advantageously, these indices form an invaluable estimation of the dynamic properties of the complex network formed by the cardiac variability of the subject subjected to an analysts via implementation of the method according to the invention.

The assortativity ASSOR and transitivity TRANS are defined such that:

The transitivity TRANS may be expressed by:

$$T(G) = \frac{|Tri(G)|}{|Tri(N)|}$$

Tri(G) being the set of all the triangles in the VG graph and

Tri(N) being the set of all the possible triangles considering all the nodes of the VG graph.

The assortativity ASSOR may be expressed by:

$$r = \frac{M^{-1}\Sigma_i j_i k_i - [M^{-1}\Sigma_i \frac{1}{2}(j_i+k_i)]^2}{M^{-1}\Sigma_i \frac{1}{2}(j_i^2+k_i^2) - [M^{-1}\Sigma_i \frac{1}{2}(j_i+k_i)]^2}$$

$j_i$ and $k_i$ being the degrees of the nodes at the end of the $i^{th}$ link, with i=1, ..., M links.

A degree is the number of links to each node.

For each link (i) there are two nodes that are connected thereto and $j_i$ is the degree of the first node and $k_i$ is the degree of the other node.

The modes of computation of the indices thus applied are not described in more detail because they are well known to those skilled in the art of statistical operations and of graph theory and are not themselves useful to the comprehension of the invention.

According to one variant of the embodiment of the invention, the sampling of a cardiac signal of a subject (baby), which forms a succession of (RRI) time samples respectively defining time intervals that separate two successive heartbeats, is replaced by sampling of signals representative of waves of cerebral origin (also called electroencephalographic signals). This sample representative of waves of cerebral origin is formed by means of sensors suitable for taking EEG (electroencephalogram) measurements via electrodes made of silver placed on the scalp, by way of example. The raw signals obtained by the EEG sensors are then digitally filtered by a band-stop filter of 50 Hz cut-off, then by a band-pass filter (of 0.53 Hz to 30 Hz passband). In other words, the sequence of (RRI) time samples derived from the ECG signal is replaced by an EEG signal thus filtered. According to this variant, an analysis of the (RRI) samples is carried out over a period of about 2 minutes and, by implementing the visibility-graph method on these (RRI) samples, a number of peaks visible from the central node of a window is determined, for successive windows of preset duration of 250 ms.

For each of the successive computations of visibility thus performed, the window is shifted by one sample. An index of the mean visibility over the duration of the EEG sampling is then obtained by computing a mean value of the visibility indices respectively attributed to the various windows, which mean visibility index is representative of the maturity of a baby. Advantageously, it has been observed that the more mature the infant on which the EEG sampling is carried out, the lower the value of the computed mean visibility index.

Advantageously, it is thus possible, for example, to estimate the date of conception of a fetus.

According to one embodiment of the invention, the number of points considered per window is equal to 64.

According to one embodiment of the invention, points considered in a window may be obtained by interpolation from measured samples.

According to variants, the duration of a window may be comprised between 50 ms and 1 second.

Advantageously, the ECG cardiac signal is scrutinized for the purposes of defining periods propitious to an analysis of the signal of electroencephalographic origin. Specifically, an analysis of the ECG cardiac signal allows moments at which the subject (baby) is calm to be defined, this allowing the effectiveness of an analysis according to the variant embodiment in which the RRI samples are samples of the signal of encephalic origin to be increased.

According to one embodiment of the invention, at least two indices respectively obtained from a first analysis of the ECG signal and from a second analysis of the EEG signal are combined so as to optimize the performance of the method for evaluating the maturation of a baby according to the invention.

The invention is not limited merely to the embodiments described above but also relates to any method for determining the maturation of a baby comprising converting time samples into data representative of a visibility graph (VG), determining at least one index from data representative of this visibility graph, comparing the at least one index thus determined with one or more statistical indices representative of the maturation of a plurality of babies and visually representing a distance between the at least one determined index and the plurality of statistical indices, and to any system implementing such a method.

According to one variant, the representation of the determined distance may be an audio representation.

The invention claimed is:

1. A system for determining the maturation of a baby, comprising
   a module for sampling a cardiac and/or electroencephalographic signal of said baby delivering a plurality of time samples, the plurality of samples of said cardiac signal defining time intervals that separate two successive heartbeats;
   a module for converting said plurality of time samples into data representative of a visibility graph,
   a module for determining one or more indices from said data representative of said visibility graph,
   an analyzing module for comparing said one or more determined indices with one or more statistical indices representative of the maturation of a plurality of babies,
   a module for visually representing a quantity representative of a distance between said one or more determined indices and said plurality of statistical indices.

2. The system for determining the maturation of a baby as claimed in claim 1, wherein said one or more determined indices are assortativity or transitivity indices (ASSOR, TRANS).

* * * * *